United States Patent
Vyasarao et al.

(10) Patent No.: US 8,568,290 B2
(45) Date of Patent: Oct. 29, 2013

(54) INFANT WARMER APPARATUS AND METHOD

(75) Inventors: Sreedhar Jyothigowdanapura Vyasarao, Bangalore (IN); Ramkumar Meenakshisundaram, Bangalore (IN)

(73) Assignee: General Electric Company, Schenectady, NY (US)

(*) Notice: Subject to any disclaimer, the term of this patent is extended or adjusted under 35 U.S.C. 154(b) by 173 days.

(21) Appl. No.: 13/044,651

(22) Filed: Mar. 10, 2011

(65) Prior Publication Data

US 2011/0245583 A1    Oct. 6, 2011

(30) Foreign Application Priority Data

Mar. 31, 2010  (IN) .............................. 896/CHE/2010

(51) Int. Cl.
*A61G 11/00*     (2006.01)
(52) U.S. Cl.
USPC .......................................................... 600/22
(58) Field of Classification Search
USPC ......... 119/331–328; 237/14; 600/22; 40/549, 40/560; 362/33, 319–325, 351; 378/204–209; 5/603, 905; 607/88–114; 606/2–19

See application file for complete search history.

(56) References Cited

U.S. PATENT DOCUMENTS

| | | | | |
|---|---|---|---|---|
| 5,830,123 | A * | 11/1998 | Franz et al. ...................... | 600/22 |
| 5,980,449 | A * | 11/1999 | Benson et al. ................... | 600/22 |
| 6,213,935 | B1 * | 4/2001 | Mackin et al. ................... | 600/22 |
| 7,488,107 | B2 * | 2/2009 | Tubbs ........................... | 378/205 |
| 2008/0046044 | A1 * | 2/2008 | Jahnigen et al. ............... | 607/100 |
| 2011/0124952 | A1 * | 5/2011 | Panicker ......................... | 600/22 |

* cited by examiner

*Primary Examiner* — Charles A Marmor, II
*Assistant Examiner* — Kaylee Wilson
(74) *Attorney, Agent, or Firm* — Global Patent Operation; Marc A. Vivenzio

(57) ABSTRACT

An infant warmer (10) includes a heater canopy (18) comprising a. heater (30) configured to generally uniformly distribute radiant energy over a fixed region. The heater canopy (18) may also include a lamp (32) configured to selectively generate light. The heater canopy (18) may also include a stencil (34) positioned relative to the lamp (32) such that at least a portion of the light passes through the stencil (34) to generate a projected image (56). The projected image (56) is configured to highlight the fixed region.

10 Claims, 3 Drawing Sheets

INFANT WARMER APPARATUS AND METHOD

BACKGROUND OF THE INVENTION

The subject matter disclosed herein relates to an infant warming apparatus and method with a patient alignment feature.

Warming devices may be implemented to warm an infant and to supply the necessary heat to maintain the infant at a predetermined temperature. Infant warmers commonly have a radiant heater that is located above the infant and which thus radiates energy in the infrared spectrum to impinge upon the infant to maintain the predetermined temperature.

One problem with conventional infant warmers is that the patient must be properly aligned with the heater assembly. If the patient is misaligned relative to the heater assembly, the patient may be insufficiently heated or heated in a non-uniform manner.

BRIEF DESCRIPTION OF THE INVENTION

The above-mentioned shortcomings, disadvantages and problems are addressed herein which will be understood by reading and understanding the following specification.

In an embodiment, an infant warmer includes a heater canopy comprising a heater configured to generally uniformly distribute radiant energy over a fixed region. The heater canopy may also include a lamp configured to selectively generate light. The heater canopy may also include a stencil positioned relative to the lamp such that at least a portion of the light passes through the stencil to generate a projected image. The projected image is configured to highlight the fixed region.

In another embodiment, an infant warmer includes a heater canopy comprising a heater configured to generally uniformly distribute radiant energy over a fixed region. The heater canopy may also include a stencil defining a stencil pattern proportional to the fixed region. The heater canopy may also include a lamp configured to selectively transmit a light through the stencil such that a projected image is generated based on the stencil pattern. The projected image is configured to visibly highlight the fixed region. The infant warmer may also include a frame connected to the heater canopy. The infant warmer may also include a base connected to the frame.

In another embodiment, a method includes providing a heater and identifying a fixed region over which the heater generally uniformly distributes radiant energy. The method may also include providing a stencil defining a stencil pattern proportional to the fixed region. The method may also include transmitting a light through the stencil to generate a projected image highlighting the fixed region.

Various other features, objects, and advantages of the invention will be made apparent to those skilled in the art from the accompanying drawings and detailed description thereof.

BRIEF DESCRIPTION OF THE DRAWINGS

FIG. 5 is an isometric illustration of a wall-mounted infant warmer in accordance an embodiment.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
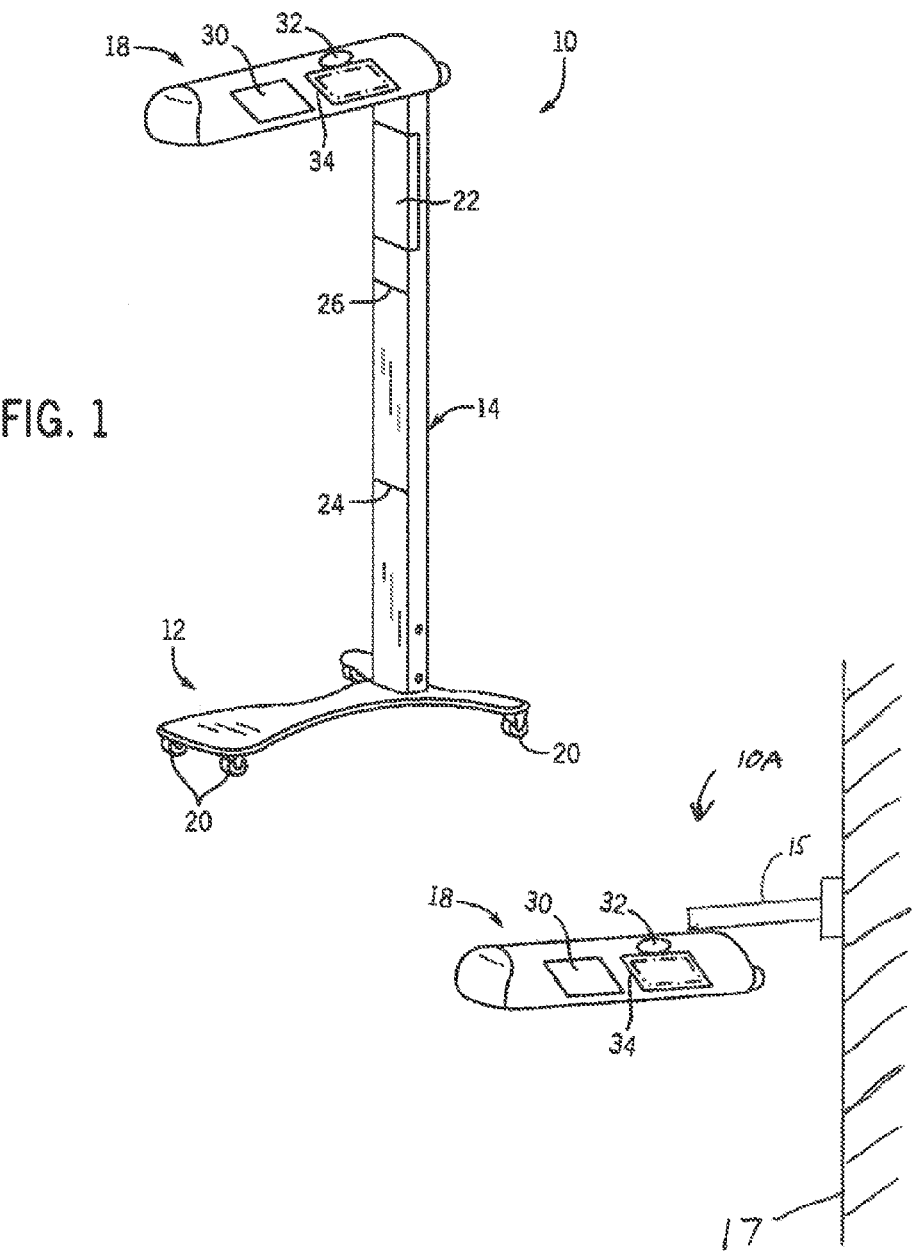
FIG. 1 is an isometric illustration of an infant warmer in accordance with an embodiment.

Referring to FIG. 1, an isometric illustration depicts an infant warmer 10 in accordance with one embodiment. The infant warmer 10 may include a base 12, a frame 14, and a heater canopy 18. It should be appreciated that the infant warmer 10 is being described in accordance with an embodiment, and that other configurations may be envisioned. As an example, according to an alternate embodiment (See FIG. 5), a wall-mounted infant warmer 10A may include a heater canopy 18 comprising a wall attachment apparatus 15 configured for direct attachment to a wall 17.

The base 12 may include a plurality of wheels 20 adapted to facilitate translation of the infant warmer 10. The frame 14 is secured to and extends away from the base 12 in a generally vertical direction. The frame 14 comprises a controller 22 configured to regulate the operation of the infant warmer 10. The frame 114 may optionally comprise one or more height adjustment marks such as the lower height adjustment mark 24 and the upper height adjustment mark 26 that are adapted to vertically position a bed 28 (shown in FIG. 4) as will hereinafter be described in more detail.

The heater canopy 18 is secured to the frame 14. The heater canopy 18 includes a heater 30, a lamp 32, and a template or stencil 34. According to one embodiment, the lamp 32 is a halogen lamp. The stencil 34 is positioned relative to the lamp 32 such that light from the lamp 32 will at least partially pass through the stencil 34 onto the bed 28 (shown in FIG. 4).

Figure 2:
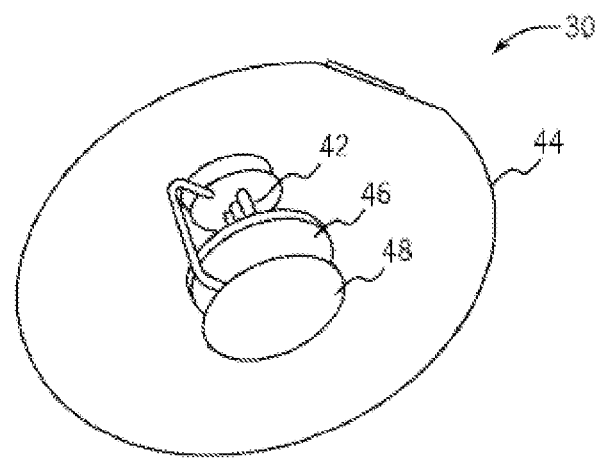
FIG. 2 is an isometric illustration of a heater in accordance with an embodiment.

Referring to FIG. 2, a detailed isometric view of the heater 30 is shown in accordance with an embodiment. The heater 30 will hereinafter be described as a radiant heater device configured to provide radiant energy in the infrared spectrum to impinge upon an infant. It should, however, be appreciated that the infant warmer 10 (shown in FIG. 1) could be configured to implement a variety of different heater types and configurations. According to the depicted embodiment, the radiant heater 30 includes an infrared emitter 42 that provides the infrared radiation that is reflected towards an infant by means of a reflector 44. The reflector 44 is preferably of a particular geometric configuration such as an ellipsoid, a paraboloid or a hyperboloid. A deflector 46 may be used to deflect sonic of the infrared energy otherwise directed toward an infant back toward and then re-reflected from the reflector 44. A heat shield 48 may be mounted on the downward side of the deflector 44 to prevent the high temperature of the deflector 44 from being accessible by the user.

Figure 3:
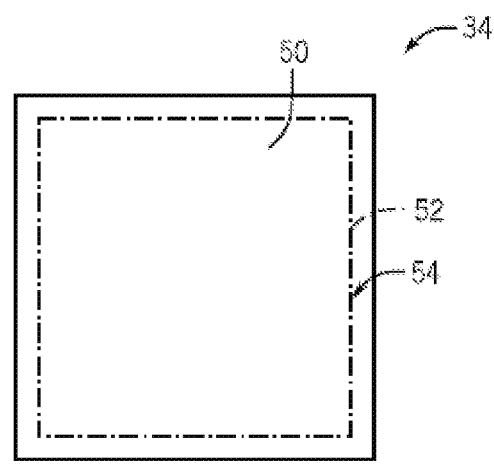
FIG. 3 is a top view of a stencil in accordance with an embodiment.

Referring to FIG. 3, a top view of the stencil 34 is shown in accordance with an embodiment. The stencil 34 may comprise a transparent portion 50 and an opaque portion 52 configured to define a predetermined stencil pattern 54. The transparent portion 50 is configured to transmit light from the lamp 32, while the opaque stencil portion 42 is configured to interrupt the transmission of light from the lamp 32. Configuring the transparent and opaque portions 50, 52 of the stencil 34 in the manner described will have the effect of generating a projected image 56 (shown in FIG. 4) when illuminated by the lamp 32. It should be appreciated that the projected image 56 is directly proportional to the stencil pattern 54. Stencils are well known in the art and therefore will not be described in further detail.

Figure 4:
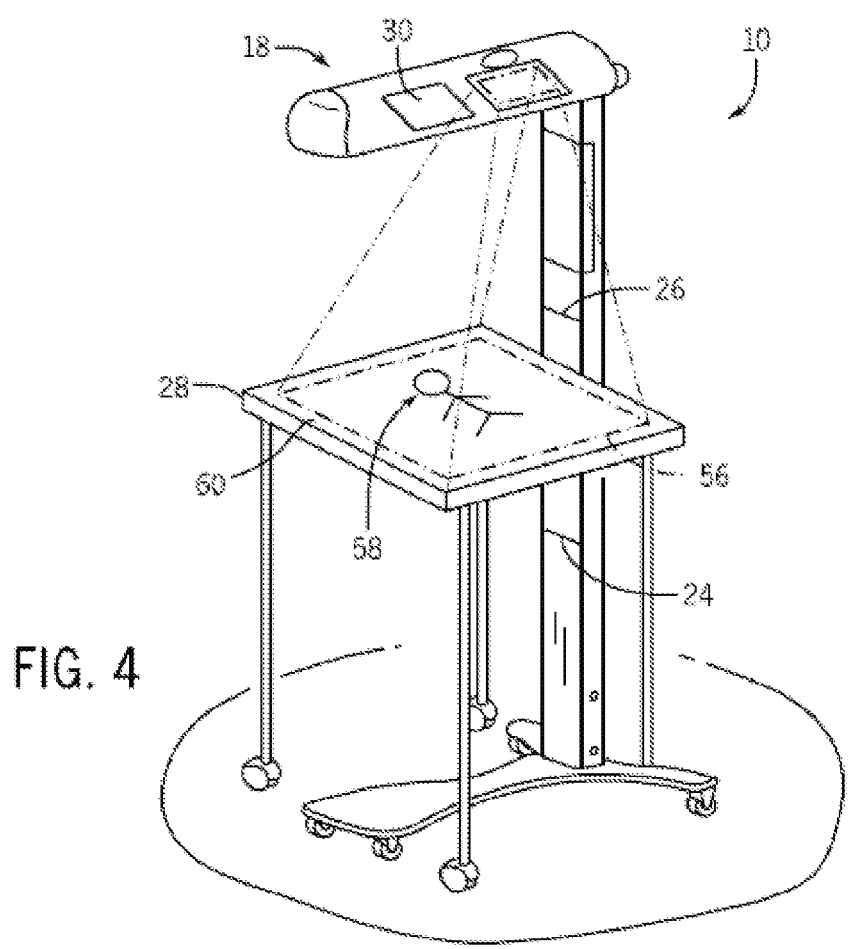
FIG. 4 is an isometric illustration of the infant warmer of FIG. 1 and a bed in accordance with an embodiment.

Referring to FIG. 4, an isometric illustration depicts the infant warmer 10 and the bed 28 in accordance with one embodiment. To ensure the infant patient 58 is sufficiently and uniformly warmed, the patient 58 must be appropriately positioned relative to the heater canopy 18 in both a horizontal and vertical direction. To vertically position the patient 58 relative to the heater canopy 18, a top surface 60 of the bed 28 should be positioned vertically between the two height adjustment marks 24, 26. In other words, a bed 28 falling below the tower height adjustment mark 24 is too far away from the heater canopy 18 and requires vertical adjustment in the upward direction. Similarly, a bed 28 rising above the upper height adjustment mark 26 is too close to the heater canopy 18 and requires vertical adjustment in the downward direction.

For purposes of horizontally positioning the patient 58 relative to the heater canopy 18, it is important to understand that the heater reflector 44 (shown in FIG. 2) is configured to uniformly distribute radiant energy over a fixed region within which the patient 58 will be sufficiently and uniformly warmed. This fixed region may be identified, for example, based on the performance characteristics of the heater 30 components or through the use of a device adapted to measure temperature such as a thermometer or a thermistor. Having identified this fixed region, the stencil pattern 54 (shown in FIG. 3) defined by the stencil 34 is selected such that the resultant projected image 56 aligns with the outer periphery of the fixed region to visibly highlight the fixed region. In other words, the stencil pattern 54 is configured to be proportional to the fixed region so that the projected image 56 circumscribes or otherwise highlights the fixed region. In this manner, any infant patient placed within the region defined by the projected image 56 will necessarily be horizontally aligned relative to the heater canopy 18.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. An infant warmer for use adjacent a bed for supporting an infant, the infant warmer comprising:
   a heater canopy comprising;
   a heater configured to generally uniformly distribute radiant energy over a fixed region of a bed for supporting an infant, the bed being positionable adjacent the heater canopy;
   a lamp configured to selectively generate light;
   a stencil positioned relative to the lamp such that at least a portion of said light passes through the stencil to generate a projected image onto the bed; and
   wherein the lamp and the stencil are cooperatively arranged so that the projected image identifies a periphery of the fixed region on the bed for positioning the infant within the fixed region to warm the infant.

2. The infant warmer of claim 1, wherein the heater canopy includes a wall attachment apparatus configured to secure the heater canopy to a wall.

3. The infant warmer of claim 1, further comprising a frame connected to the heater canopy.

4. The infant warmer of claim 3, wherein the frame includes a height adjustment mark configured to vertically position the infant relative to the heater.

5. The infant warmer of claim 1, wherein the stencil comprises a transparent portion and an opaque portion.

6. The infant warmer of claim 5, wherein the opaque portion of the stencil defines a stencil pattern configured to produce the projected image.

7. An infant warmer for use adjacent a bed for supporting an infant, the infant warmer comprising:
   a heater canopy comprising
   a heater configured to generally uniformly distribute radiant energy over a fixed region of a bed for supporting an infant, the heater canopy being positionable adjacent the bed;
   a stencil defining a stencil pattern proportional to the fixed region; and
   a lamp configured to selectively transmit a light through the stencil such that a projected image is generated based on the stencil pattern, said projected image configured to visibly highlight the fixed region on the bed;
   a frame connected to the heater canopy;
   a base connected to the frame, the base being movable relative to the bed for positioning the heater relative to the bed; and
   wherein the lamp and the stencil are cooperatively configured so that the projected image identifies a periphery of the fixed region on the bed for positioning the infant within the fixed region to warm the infant.

8. The infant warmer of claim 7, wherein the frame includes a height adjustment mark configured to vertically position the infant relative to the heater.

9. The infant warmer of claim 7, wherein the base comprises a plurality of wheels adapted to facilitate translation of the infant warmer.

10. The infant warmer of claim 7, wherein the stencil comprises a transparent portion and an opaque portion.

* * * * *

UNITED STATES PATENT AND TRADEMARK OFFICE
CERTIFICATE OF CORRECTION

PATENT NO. : 8,568,290 B2
APPLICATION NO. : 13/044651
DATED : October 29, 2013
INVENTOR(S) : Vyasarao et al.

Page 1 of 1

It is certified that error appears in the above-identified patent and that said Letters Patent is hereby corrected as shown below:

On the Title Page, Item (57), under "ABSTRACT", in Column 2, Line 2, delete "a." and insert -- a --, therefor.

In the Specification

In Column 2, Line 4, delete "accordance" and insert -- accordance with --, therefor.

In Column 2, Line 34, delete "frame 114" and insert -- frame 14 --, therefor.

In Column 2, Line 58, delete "sonic" and insert -- some --, therefor.

In Column 2, Line 61, delete "the deflector 44 to" and insert -- the deflector 46 to --, therefor.

In Column 2, Lines 61-62, delete "deflector 44" and insert -- deflector 46 --, therefor.

In Column 3, Line 19, delete "tower" and insert -- lower --, therefor.

In the Claims

In Column 3, Line 58, in Claim 1, delete "comprising;" and insert -- comprising: --, therefor.

In Column 4, Line 30, in Claim 7, delete "comprising" and insert -- comprising: --, therefor.

Signed and Sealed this
Eleventh Day of February, 2014

Michelle K. Lee
*Deputy Director of the United States Patent and Trademark Office*